US008883165B2

(12) United States Patent
Kaminaka et al.

(10) Patent No.: US 8,883,165 B2
(45) Date of Patent: Nov. 11, 2014

(54) MODIFIED PEPTIDE VACCINE DERIVED FROM INFLUENZA M2

(75) Inventors: Kazuyoshi Kaminaka, Kikuchi (JP); Chikateru Nozaki, Kikuchi (JP); Junichi Matsuda, Kikuchi (JP); Kiyoto Nishiyama, Kikuchi (JP)

(73) Assignee: The Chemo-Sero-Therapeutic Research Institute, Kumamoto-shi (JP)

( * ) Notice: Subject to any disclaimer, the term of this patent is extended or adjusted under 35 U.S.C. 154(b) by 21 days.

(21) Appl. No.: 13/392,994

(22) PCT Filed: Aug. 23, 2010

(86) PCT No.: PCT/JP2010/064166
§ 371 (c)(1),
(2), (4) Date: May 25, 2012

(87) PCT Pub. No.: WO2011/024748
PCT Pub. Date: Mar. 3, 2011

(65) Prior Publication Data
US 2012/0244184 A1  Sep. 27, 2012

(30) Foreign Application Priority Data

Aug. 28, 2009  (JP) .................. 2009-197564
Mar. 16, 2010  (JP) .................. 2010-058577

(51) Int. Cl.
A61K 39/12      (2006.01)
A61K 39/00      (2006.01)
A61K 39/385     (2006.01)
A61K 39/145     (2006.01)
A61K 38/00      (2006.01)
C07K 17/00      (2006.01)
C07K 14/005     (2006.01)

(52) U.S. Cl.
CPC .............. A61K 39/145 (2013.01); A61K 39/00 (2013.01); C12N 2760/16122 (2013.01); C07K 14/005 (2013.01); A61K 2039/55505 (2013.01); C12N 2760/16134 (2013.01)
USPC ................... 424/186.1; 424/192.1; 424/193.1; 424/204.1; 424/209.1; 530/300; 530/325

(58) Field of Classification Search
CPC ............. C07K 14/005; C07K 2319/00; C12N 2760/16122; C12N 2760/16134; C12N 2760/16222; C12N 2760/16234; C12N 2760/16022; C12N 2760/16123; C12N 2760/16142; C12N 2760/16151; A61K 39/145; A61K 2039/5258; A61K 2039/6075; A61K 39/12
See application file for complete search history.

(56) References Cited

U.S. PATENT DOCUMENTS 6,169,175 B1  1/2001  Frace et al.

FOREIGN PATENT DOCUMENTS

JP   2001-512748        8/2001
WO   WO 99/07839        2/1999
WO   WO 2004056852  *   7/2004
WO   WO 2006/034255 A2  3/2006
WO   WO 2007078879  *   7/2007
WO   WO 2008/133208 A1  11/2008

OTHER PUBLICATIONS

Wizemann et al. Polyhistidine-tagged hepatitis B core particles as carriers of HIV-1/gp 120 epitopes of different HIV-1 subtypes. Biological Chemistry, 2000, vol. 381, p. 231-243.*
Damme et al. Safety and efficacy of a novel microneedle device for dose sparing intradermal influenza vaccination in healthy adults. Vaccine, 2009, vol. 27, p. 454-459.*
Liu, W., et al., "Monoclonal antibodies recognizing EVETPIRN epitope of influenza A virus M2 protein could protect mice from lethal influenza A virus challenge," Immunology Letters, vol. 93, pp. 131-136, (Apr. 13, 2004).
Matsuda, J., et al., "Amyloid B peptides with an additional cysteine residue can enhance immunogenicity and reduce the amyloid B burden in an Alzheimer's disease mouse model," Biochemical and Biophysical Research Communications, vol. 382, pp. 149-152, (Mar. 2009).
De Filette, M., et al., "Universal influenza A vaccine: Optimization of M2-based constructs," Virology, vol. 337 pp. 149-161, (May 3, 2005).
Zhang, M., et al., "Fine specificity and sequence of antibodies directed against the ectodomain of matrix protein 2 of influenza A virus," Molecular Immunology, vol. 43, pp. 2195-2206, (Feb. 10, 2006).
Beachey, E.H., et al., "Epitope-specific protective immunogenicity of chemically synthesized 13-, 18-, and 23-residue peptide fragments of steptococcal M protein," Proceedings of the National Academy of Science USA, vol. 81, pp. 2203-2207, (Apr. 1984).

(Continued)

Primary Examiner — Benjamin P Blumel
(74) Attorney, Agent, or Firm — Oblon, Spivak, McClelland, Maier & Neustadt, L.L.P.

(57) ABSTRACT

A modified peptide derived from matrix protein 2 (hereinafter also referred to as "M2"), one of surface layer proteins of influenza virus, and a method for utilization of the modified peptide are provided. A peptide (hereinafter also referred to as "M2eC peptide") that is made up by inserting cysteine residue(s) into a peptide (hereinafter also referred to as "M2e") consisting of 23 amino acid residues of from positions No. 2 to No. 24 of M2 in influenza virus type A, a fusion protein consisting of said modified peptide and a polypeptide, an influenza vaccine comprising said modified peptide or said fusion protein as an active ingredient, a device which can be delivered into the body comprising said influenza vaccine, a nucleic acid fragment consisting of a nucleotide sequence encoding the amino acid sequence of said modified peptide or said fusion protein, an expression vector in which said nucleic acid fragment is incorporated, a host in which said expression vector is introduced, and an antibody that has a protective effect against influenza virus.

10 Claims, 3 Drawing Sheets

(56) References Cited

OTHER PUBLICATIONS

International Search Report Issued Sep. 14, 2010 in PCT/JP10/64166 Filed Aug. 23, 2010.

Vladimir A. Slepushkin, et al., "Protection of mice against influenza A virus challenge by vaccination with baculovirus-expressed M2 protein", Vaccine, vol. 13, No. 15, 1995, pp. 1399-1402.

Suzanne L. Zebedee, et al., "Influenza A Virus $M_2$ Protein: Monoclonal Antibody Restriction of Virus Growth and Detection of $M_2$ in Virions", Journal of Virology, vol. 62, No. 8, Aug. 1988, pp. 2762-2772.

Robert A. Lamb, et al., "Influenza Virus $M_2$ Protein Is an Integral Membrane Protein Expressed on the Infected-Cell Surface", Cell, vol. 40, Mar. 1985, pp. 627-633.

Patsy G. Hughey, et al., "Effects of Antibody to the Influenza A Virus M2 Protein on M2 Surface Expression and Virus Assembly", Virology, vol. 212, 1995, pp. 411-421.

John J. Treanor, et al., "Passively Transferred Monoclonal Antibody to the M2 Protein Inhibits Influenza A Virus Replication in Mice", Journal of Virology, vol. 64, No. 3, Mar. 1990, pp. 1375-1377.

Sabine Neirynck, et al., "A universal influenza A vaccine based on the extracellular domain of the M2 protein", Nature Medicine, vol. 5, No. 10, Oct. 1999, pp. 1157-1163.

Fan Wu, et al., "Characterization of immunity induced by M2e of influenza virus", Vaccine, vol. 25, 2007, pp. 8868-8873.

Krystyna Mozdzanowska, et al., "Roles of adjuvant and route of vaccination in antibody response and protection engendered by a synthetic matrix protein 2- based influenza A virus vaccine in the mouse", Virology Journal, vol. 4, No. 118, 2007, 14 pages.

The Extended European Search Report issued Apr. 5, 2013, in Application No. / Patent No. 10811798.7-1412 / 2471915 PCT/JP2010064166.

Roxana M. Ionescu, et al., "Pharmaceutical and Immunological Evaluation of Human Papillomavirus Viruslike Particle as an Antigen Carrier", Journal of Pharmaceutical Sciences, vol. 95, No. 1, XP002685352, Jan. 1, 2006, pp. 70-79.

U.S. Appl. No. 14/018,495, filed Sep. 5, 2013, Matsuda, et al.

\* cited by examiner

MODIFIED PEPTIDE VACCINE DERIVED FROM INFLUENZA M2

This application is a National Stage of PCT/JP10/064,166 filed Aug. 23, 2010 and claims the benefit of JP 2009-197564 filed Aug. 28, 2009 and JP 2010-058577 filed Mar. 16, 2010.

TECHNICAL FIELD

The present invention relates to a modified peptide which is made up by inserting cysteine residue(s) into a peptide consisting of a portion of matrix protein 2 in influenza virus and a method for utilization of the modified peptide.

BACKGROUND ART

Influenza virus belongs to the family Orthomyxoviridae family and is a negative strand, single-stranded RNA virus. The size of the viral particle is 80 to 120 nm. The viral particle has erythrocyte agglutinin (hemagglutinin, HA), neuraminidase (NA) and matrix protein (M2) in the lipid bilayer membrane of surface layer, which is lined with matrix protein 1 (M1). A segmented negative strand RNA within the surface layer forms a complex (RNP) with a nuclear protein (NP) and an RNA polymerase (PA, PB1, PB2). Influenza virus is classified into type A, B or C depending on antigenicity of the internal protein, among which type A and type B may cause an epidemic of influenza in human. It is type A that may cause a pandemic of influenza with potent pathogenicity. For type A influenza virus, it is known that there are many serotypes resulting from combination of 16 subtypes for HA and 9 subtypes for NA.

It is known that, in general, an RNA virus is susceptible to mutation. Influenza virus is not an exception and its antigenicity has been changed by degrees year by year through point mutation of a gene encoding HA or NA (antigen drift). For influenza virus type A, it is known that an antigenically different new virus strain develops by discrete mutation replacing either or both of HA and NA with another subtype(s) at an interval of several decades (antigen shift). Influenza viral mutation by such antigen drift and/or shift continually causes damages to human. In the past, several shifts of antigenicity had occurred in the world, to cause epidemic (pandemic) producing many victims. Specifically, there were Spanish flu in 1918, Asian flu in 1957, Hong-Kong flu in 1968 and Russian flu in 1977.

Influenza caused by infection of influenza virus is one of serious infectious diseases which occur in epidemics on a worldwide scale. There have been many cases of death or encephalitis in the aged, children or patients with a weak immune system. Even if influenza virus infection does not result in death in patients, physical symptoms such as fever, headache and fatigue, may force patients to stop social activities for a certain period of time resulting in great economic loss. Thus, there is a need for establishing an effective preventive measure against even a new virus strain, because of increased likelihood of occurrence of a new virus strain by shift of antigenicity in addition to importance of conventional protection against influenza virus infection.

A preventive measure against influenza is to perform vaccination every year. Vaccines currently in practical usage are split vaccines which comprise as a main ingredient HA purified from a strain for preparation of a vaccine cultured with chicken embryonated eggs. Thus, a virus predicted to occur in epidemics in the year is used as a strain for preparation of a vaccine. It is therefore necessary to determine a strain for preparation of a vaccine every year by predicting a strain causing epidemics, and in case of mismatch between a strain for preparation of a vaccine and a strain causing epidemics, the vaccine would be less effective. As compared to vaccines giving immunity over at least several years with a single vaccination schedule such as DPT (diphtheria, pertussis, tetanus) vaccine and Japanese encephalitis vaccine, current influenza vaccines need vaccination every year and therefore are inconvenient for both those who receive the vaccine and physicians who inject the vaccine and would be a burden of the expense. Furthermore, in case of occurrence of a different virus strain from an expected virus strain due to failure in the prediction in epidemics, those who receive the vaccine would still be infected with influenza virus in spite of vaccination. In particular, in case of occurrence of a new strain of influenza generated by shift resulting in significantly different antigenicity, since protective effects would scarcely be expected with the conventional influenza vaccines, explosive prevalence of the virus would result, so-called pandemic.

As described above, since current influenza vaccines can not sufficiently cope with mutation in the virus, a universal influenza vaccine less affected by antigenic mutation is highly desired to resolve such problem.

Since influenza virus causing such epidemic is influenza virus type A, a desired influenza vaccine against not only annual epidemic but also pandemic would be obtained by developing a vaccine that provides immunogenicity common in influenza virus type A. From such a point of view, research of a vaccine which targets a M2 protein common in influenza virus type A has been performed (See, for example, Non-patent reference 1). The M2 protein is a viral surface protein with a relatively well-conserved amino acid sequence among influenza virus type A. It is present in a relatively small amount in influenza virus particles (See, for example, Non-patent reference 2) but is expressed at a relatively high level in virus-infected cells (See, for example, Non-patent reference 3).

It has been reported that an antibody against M2 inhibits the replication of influenza virus type A both in in vivo and in vitro models (See, for example, Non-patent references 4 and 5). Further, Slepushkin et al., have reported that, in mice inoculated with M2, fatal infection by heterologous influenza virus type A is prevented and removal of the virus from the lung tissue is facilitated (See, for example, Non-patent reference 1). It has also been reported that a modified M2 protein in which a hydrophobic transmembrane domain is eliminated is useful for preparation of a vaccine (See, for example, Patent reference 1).

On the other hand, Neirynck et al., have reported that an extracellular domain of M2 fused to the N-terminal of a hepatitis B virus core antigen is used as a vaccine antigen (See, Non-patent reference 6). According to Neirynck et al., a hepatitis B virus core particle exposing M2 onto its surface is expressed in E. coli, the particle is purified from the E. coli, and an antibody against M2 is induced by administering the particle together with adjuvant.

Also, with an experiment using mice, Wu et al. (See, for example, Non-patent reference 7) and Mozdzanowska et al. (See, for example, Non-patent reference 8) have reported that a peptide (M2e) which corresponds to a region consisting of 23 amino acid residues generated after removal of a hydrophobic transmembrane domain from M2 also be able to protect the fatal infection by heterologous influenza virus type A by utilizing adjuvant or a peptide of oligomer called MAP. It is also revealed that at least one of epitopes against protective antibody produced by immunization with M2e is present in an amino acid region of from positions No. 6 to No. 13 of M2e (See, for example, Non-patent reference 9).

Preparation of the conventional influenza vaccines required time-consuming and laborious processes, i.e. first predicting a strain of virus prevalent in the year, adapting the virus to culture in eggs, culturing the virus in a large number of eggs, isolating the virus from the culture, inactivating the virus, and purifying an antigen protein. Development of a new vaccine that makes it unnecessary to predict a virus strain prevalent in the year so as to prepare a vaccine strain and that may cope with pandemic would greatly contribute to national welfare and reduce medical expense.

Patent reference 1: U.S. Pat. No. 6,169,175
Patent reference 2: JP-A-2001-512748
Non-patent reference 1: Slepushkin et al., 1995, Vaccine 13: p 1399-1402
Non-patent reference 2: Zebedee and Lamb, 1988 J. Virol. 62: p 2762-2772
Non-patent reference 3: Lamb et al., 1985 Cell 40: p 627-633
Non-patent reference 4: Hughey et al., 1995 Virology 212: p 411-421
Non-patent reference 5: Treanor et al., 1990 J. Virol. 64: p 1375-1377
Non-patent reference 6: 1999 Nature Med. 5: p 1157-1163
Non-patent reference 7: 2007 Vaccine 25: p 8868-8873
Non-patent reference 8: 2007 Virology J. 4: 118 doi: 10.1186/1743-422X-4-118
Non-patent reference 9: Wanli et al., 2004 Immunol. Lett 93: p 131-136

DISCLOSURE OF THE INVENTION

Technical Problem to be Solved by the Invention

An object of the present invention is to provide a modified peptide having potent immunogenicity derived from matrix protein 2 (hereinafter also referred to as "M2"), one of surface layer proteins of influenza virus, and a method for utilization of the modified peptide.

Means for Solving the Problems

Under the circumstances, the present inventors have continued research assiduously so as to attain the object described above and as a consequence have found that a peptide (hereinafter also referred to as "M2eC peptide") that is made up by inserting cysteine residue(s) into a peptide (hereinafter also referred to as "M2e") consisting of 23 amino acid residues of from positions No. 2 to No. 24 of M2 in influenza virus type A has much higher immunogenicity (twice to 20 times higher) than M2e hitherto reported to thereby complete the present invention.

In accordance with the present invention, M2eC peptide which is made up by inserting cysteine residue(s) into a peptide (M2e) consisting of 23 amino acid residues of from positions No. 2 to No. 24 of M2 (See, Patent reference 2), said M2 consisting of 97 amino acid residues and being one of surface layer proteins; a fusion protein of M2eC peptide and other polypeptide; an influenza vaccine comprising M2eC peptide or the fusion protein as an active ingredient; a nucleic acid fragment consisting of a nucleotide sequence encoding the amino acid sequence of M2eC peptide or the fusion protein; an expression vector (including a virus vector) in which the nucleic acid fragment is incorporated; and a host in which the expression vector is introduced and an antibody recognizing M2 are provided.

The M2eC peptide and the nucleic acid fragment consisting of a nucleotide sequence encoding the amino acid sequence of the M2eC peptide may effectively be utilized for prevention and treatment of influenza infection. Thus, the present invention includes the following:

[1] A modified peptide which is made up by inserting cysteine residue(s) into a peptide consisting of an amino acid sequence of from positions No. 2 to No. 24 of matrix protein 2 in influenza virus (M2e).

[2] The modified peptide of [1], wherein influenza virus is influenza virus type A.

[3] The modified peptide of [1] or [2], wherein said cysteine residue(s) is/are inserted at position between No. and No. 16 of M2e or at the C-terminal to position between No. 15 and No. 16 of M2e.

[4] The modified peptide of [3], wherein said cysteine residue(s) is/are inserted at either one or a combination of two or more of positions between No. 15 and No. 16, between No. 20 and No. 21, between No. 21 and No. 22, between No. 22 and No. 23 and between No. 23 and No. 24 of M2e.

[5] The modified peptide of any one of [1] to [4], wherein a total number of said cysteine residue(s) inserted is 1 to 5.

[6] The modified peptide of [5], wherein the number of inserted cysteine residue(s) on said each inserted position is up to 3.

[7] A fusion protein consisting of the modified peptide of any one of [1] to [6] and a polypeptide.

[8] The fusion protein of [7], wherein the polypeptide is annexin V or albumin.

[9] An influenza vaccine comprising the modified peptide of any one of [1] to [6] or the fusion protein of [7] or [8] as an active ingredient.

[10] A device which can be delivered into the body across a biological barrier, said device comprising the influenza vaccine of [9].

[11] A nucleic acid fragment consisting of a nucleotide sequence encoding the amino acid sequence of the modified peptide of any one of [1] to [6] or the fusion protein of [7] or [8].

[12] An expression vector in which the nucleic acid fragment of [11] is incorporated.

[13] A host in which the expression vector of [12] is introduced.

[14] An antibody that recognizes the modified peptide of any one of [1] to [6] and has a protective effect against influenza virus.

More Efficacious Effects than Prior Art

The M2eC peptide of the present invention has an ability of producing an effective antibody for prevention of influenza virus infection twice to 20 times higher than that of M2e with no insertion of cysteine residue(s). For example, M2eC peptide consisting of an amino acid sequence of Ser-Leu-Leu-Thr-Glu-Val-Glu-Thr-Pro-Ile-Arg-Asn-Glu-Trp-Gly-Cys-Arg-Cys-Asn-Cys-Asp-Cys-Ser-Cys-Ser-Asp (SEQ ID No: 10), which is one embodiment of the M2eC peptide of the present invention, has about 20 times higher immunogenicity than that of M2e as hitherto reported and may suitably be used for an influenza vaccine. In addition, the 9 amino acid residues at the N-terminal of the M2eC peptide of the present invention have an amino acid sequence well-conserved among influenza viruses, and thus the peptide is independent of a prevalent strain. Furthermore, the peptides of such size may be synthesized homogeneously in a large amount at a lower price by chemical synthesis, which would be great advantage for prompt supply of a vaccine in emergency of pandemic. The M2eC peptide of the present invention may also be expressed as a fusion with other polypeptide.

BEST MODE FOR CARRYING OUT THE INVENTION

Figure 1:
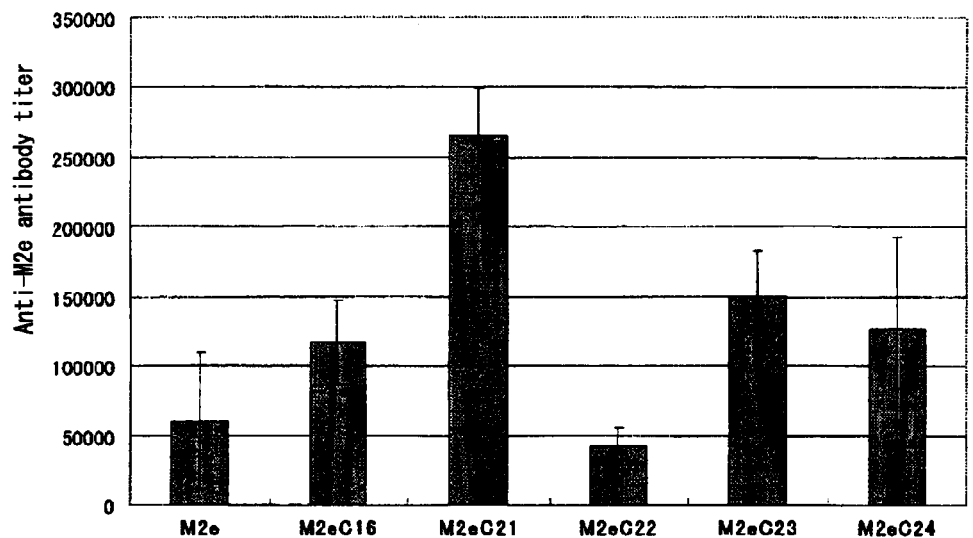
FIG. 1 is a graph showing mean anti-M2e antibody titers of the respective immunization groups shown in Table 2.

The present invention features a peptide which is made up by inserting cysteine residue(s) into 23 amino acid residues consisting of an amino acid sequence of from positions No. 2 to No. 24 of matrix protein 2 in influenza virus (M2e) (M2eC peptide).

The M2e used in the M2eC peptide of the present invention may be derived from any strain of type A influenza virus which has an ability of producing a protective antibody against influenza virus. For type A influenza virus, many serotypes resulting from combination of 16 subtypes for HA and 9 subtypes for NA have been isolated. Such serotypes include, as reported, A/PR/8 strain, IOWA strain, WISC strain, TAIW strain, LENT strain, VIET strain, INDO strain, HK156 strain, A/Beijing/262/95 strain, A/Sydney/5/97 strain, A/Panama/2007/99 strain, A/Wyoming/3/2003 strain, A/New Caledonia/20/99 strain, A/New York/55/2004 strain, A/Hiroshima/52/2005 strain, A/Solomon Islands/3/2006 strain, A/Brisbane/59/2007 strain, A/Uruguay/716/2007 strain, and A/California/05/2009 and A/California/06/2009, M2e derived from M2 in any of which strain may be used.

Preferably, M2e consisting of an amino acid sequence represented by the following formula: Ser-X1aa-Leu-Thr-Glu-Val-Glu-Thr-Pro-X2aa-Arg-X3aa-X4aa-Trp-X5aa-Cys-X6aa-Cys-X7aa-X8aa-Ser-X9aa-Asp wherein X1aa is Pro or Leu, X2aa is Ile or Thr, X3aa is Asn or Ser, X4aa is Gly or Glu, X5aa is Gly or Glu, X6aa is Lys or Arg, X7aa is Asn or Ser, X8aa is Gly or Asp and X9aa is Asn or Ser (SEQ ID No: 20) may be used. Said X1aa, X2aa, X3aa, X4aa, X5aa, X6aa, X7aa, X8aa and X9aa are those resulting from substitution of amino acids derived from the above serotypes. Most preferably, M2e consisting of the amino acid sequence of Ser-Leu-Leu-Thr-Glu-Val-Glu-Thr-Pro-Ile-Arg-Asn-Glu-Trp-Gly-Cys-Arg-Cys-Asn-Asp-Ser-Ser-Asp (SEQ ID No: 1) may be used.

Positions and numbers of cysteine residue(s) to be inserted in M2e are not specifically limited insofar as important epitope regions involved in production of a protective antibody may not be affected. In order to provide a potent immunity against influenza virus infectious disease, one to five cysteine residue(s) may be inserted at any position(s) between No. 15 and No. 16, between No. 20 and No. 21, between No. 21 and No. 22, between No. 22 and No. 23 and between No. 23 and No. 24 of M2e. Preferably, each one cysteine residue, four in total, may be inserted at positions between No. 20 and No. 21, between No. 21 and No. 22, between No. 22 and No. 23 and between No. 23 and No. 24 of M2e. Also, up to three cysteine residues may be inserted in at least one of said respective positions described above. Preferably, three cysteine residues are inserted at position between No. 20 and No. 21 of M2e.

The M2eC peptide of the present invention may be obtained by chemical synthesis with a peptide synthesizer (for example, 430A peptide synthesizer: PerkinElmer Japan Co., Ltd., Applied Biosystems) on the basis of an amino acid sequence predicted from the nucleotide sequence of M2 protein derived from various influenza viruses hitherto reported (See, for example, Non-patent reference 5) and the design relating to insertions of cysteine residue(s) described above. Currently, there are many peptide synthesis contractors, for example, BEX CO., LTD, Toray Research Center, inc., TAKARA BIO Inc., and Invitrogen, and thus their synthesis can be entrusted to them.

The M2eC peptide of the present invention may be used as a fusion protein in conjunction with various polypeptides such as albumin, annexin V and virus protein (HBV core protein etc.). Said polypeptide is not specifically limited but preferably one which is expressed in a selected host at a higher level. The nucleic acid fragment encoding said polypeptide may be obtained by utilizing gene recombination technique by Sambrook et al. (Molecular Cloning, A Laboratory Manual Second Edition. Cold Spring Harbor Laboratory Press, N.Y., 1989). A nucleic acid fragment encoding a fusion protein may be prepared by linking the nucleic acid fragment encoding the M2eC peptide of the present invention to a nucleic acid fragment encoding other polypeptide with PCR or a process using a DNA synthetase. For example, when a nucleic acid fragment encoding a fusion protein is obtained with PCR, a primer consisting of the nucleotide sequence encoding the M2eC peptide of the present invention and the nucleotide sequence (21 nucleotides) encoding a portion of the polypeptide to be fused and another primer for the polypeptide to be fused (a direction of each primer may be determined by either of which polypeptide is positioned on the N-terminal) may be used. A nucleotide sequence of cleavage site for proper restriction enzyme may be inserted or added to the terminal of a primer.

The thus obtained nucleic acid fragment encoding the M2eC peptide or the fusion protein of the present invention may be incorporated into a desired expression vector and the vector may be introduced into a host for expression of the nucleic acid fragment. A plasmid and a virus vector may be used as an expression vector. A promoter to be incorporated in said expression vector may be selected from a promoter such as Lac, tac, pho5, adh, SV40 early, SV40 late, β-actin, depending on microorganisms or animal cells used as a host. Bacteria, yeast, animal cells, plant cells and insect cells may usually be used as a host but may be selected depending on a purpose of use. For transformation of a host cell, a known procedure may be utilized. For example, calcium phosphate, DEAE dextran, liposome of lipofectin system, protoplast polyethylene glycol fusion and electroporation may be utilized, and a desired method may be selected depending on a host cell used.

Purification of the M2eC peptide and the fusion protein of the present invention may be accomplished by suitably combining methods usually used in protein chemistry such as, for example, centrifugation, salting-out, ultrafiltration, isoelectric precipitation, electrophoresis, ion-exchange chromatography, gel filtration chromatography, affinity chromatography, hydrophobic chromatography, hydroxyapatite chromatography, and the like.

Furthermore, for the purpose of facilitating purification of M2eC peptide of the present invention, the peptide may be expressed as a fusion with other polypeptide or peptide. A vector expressing such fusion protein includes His-tag expression system adding oligohistidine (Novagen), a system expressing a fusion protein to which FLAG tag is added (Sigma), glutathione S transferase (GST) fusion protein purification system preparing a fusion protein with GST (GE Healthcare Bioscience), MagneHis Protein Purification System (Promega Inc), and the like. For example, the M2eC peptide of the present invention may be expressed as a fusion peptide with oligohistidine and then the peptide may be specifically and easily purified by using nickel affinity column (GE Healthcare Bioscience).

An amount of the obtained M2eC peptide may be determined by gravimetry with a balance and ultraviolet spectrometry (spectrometry at wavelength of 214 nm). An amount of the fusion protein with the M2eC peptide may be determined by BCA Protein Assay Reagent Kit (Pierce Biotechnology, Inc), Protein Assay Kit (Bio-Rad Japan, Inc) etc.

Evaluation as a vaccine of the M2eC peptide and the fusion protein of the M2eC peptide and other polypeptide of the present invention (hereinafter also referred simply to as "antigen") may be performed by immunizing small animals such as chicken, mouse, rat, guinea pig, dog or monkey with the antigen, and then obtaining blood from the immunized animal, isolating serum therefrom, and determining an antibody titer against the M2eC peptide of the present invention or a neutralizing antibody titer against an influenza virus in said serum in in vitro system, or by administering a lethal dose of influenza virus to said immunized animal, and then observing life and death or disease conditions of the immunized animal in in vivo system. For a measurement of antibody in in vitro system, ELISA, PHA or plaque assay may be commonly used. The thus obtained M2eC peptide of the present invention has an ability of producing an effective antibody for inhibiting an infection of influenza virus twice to 20 times higher than that of M2e, and may be utilized as an immunizing antigen of an influenza vaccine. When used as an immunizing antigen of an influenza vaccine, a single M2eC peptide may be used, or two or more M2eC peptides or the M2eC peptide(s) in combination with other influenza virus antigens such as HA, NA and NP antigen may also be used.

Immunization protocol, for example, route of administration e.g. subcutaneously, intradermally, intramuscularly, intraperitoneally, nasally, orally and sublingually, and an interval of immunization, may be any method that may induce an immunity such as a standard immunization method commonly used for investigating immunogenicity of a vaccine or immunization using a device which can be delivered into the body across a biological barrier. Such device includes a micro needle and a hydrophilic gel patch in various forms for inducing immunity via the skin, and various enteric capsules, liposomes and non-enveloped virus particles for inducing immunity via the intestinal tract. Any adjuvant which can be used in human such as, for example, aluminum hydroxide gel, aluminum phosphate gel, CpG oligonucleotide, MDP, QS21, and MPL+TDM emulsion may be added to an antigen used for immunization so as to increase its capacity for immunization. Furthermore, for the purpose of stability or maintaining a form of an antigen, various pharmaceutically acceptable additives may be added to the antigen. Such additives include a stabilizing agent (arginine, Polysorbate 80, Macrogol 4000, etc.) and an excipient (mannitol, sorbitol, sucrose, lactose). A composition comprising the thus prepared M2eC peptide or the fusion protein of the present invention as an active ingredient may be subject to sterile filtration, dispensation, lyophilization, and the like for formulation and used as a vaccine for prevention of infection of influenza virus and onset of a disease.

As described above, the M2eC peptide of the present invention is capable of producing a protective antibody against influenza virus and the obtained antibody may be utilized as material for treating a patient suffering from influenza and material for constructing a detection system of influenza virus, for example, a detection system via antibody measure such as ELISA, Western blotting and dot blotting. Such protective antibody (polyclonal antibody) may be obtained from serum of animals immunized by the above immunization protocol. For purification of an antibody, the purification of a protein as described above may be used.

A monoclonal antibody may be obtained as described below. Namely, antibody-producing cells such as spleen cells or lymphocytes are removed from the immunized animal and fused with myeloma cell strain to prepare hybridomas, in accordance with e.g. Milstein et al., Method Enzymol., 73, 3-46, 1981. Mouse myeloma cell strains such as NSI-Ag4/1 (Eur. J. Immunol., 6:511, 1976), P3X63-Ag8.U1 (Curr. Topics Microbiol. Immunol., 81:1, 1978), X63-Ag8.653 (J. Immunol., 123:1548, 1979), and the like may be used. Hybridomas may be obtained by culture in a HAT medium for a period of time sufficient for non-fused cells to die out, usually from several days to several weeks. From the thus obtained hybridomas, those producing an antibody of interest are then selected and cloned with ordinary limiting dilution using their culture fluid. Selection of a clone producing an antibody specifically binding to the peptide of the present invention may be done with analytical techniques commonly used such as ELISA, RIA, or Western blot. An antibody binding to the M2eC peptide of the present invention may also be prepared by the technique for antibody preparation using phage display (Phage Display of Peptides and Proteins: A Laboratory Manual Edited by Brian K. Kay et al., Antibody Engineering: A PRACTICAL APPROACH Edited by J. McCAFFERTY et al., ANTIBODY ENGINEERING second edition edited by Carl A. K. BORREBAECK).

The present invention is explained in more detail by means of the following Examples but is not limited to these Examples in any way.

Example 1

Evaluation of Immunogenicity of M2eC Peptides which is Made Up by Inserting Cysteine Residue(s) into M2e 1. Materials and Methods (1) M2eC Peptide An amino acid sequence of M2e as a template for preparing M2eC peptide was synthesized based on the amino acid sequence of A/New Caledonia/20/1999(H1N1) strain (GeneBank Accession number ACF41880) having more universal sequence (1999 Nature Med. 5: 1157-1163) (BEX Co., Ltd.). The synthesized M2e and the respective M2eC peptides are shown in Table 1. The synthesized respective peptides were prepared at 5 mg/mL with distilled water for injection substituted with nitrogen gas containing 1 mM of EDTA, and stored as a stock solution at below −80° C. until use.

TABLE 1

| Abbreviations | Amino acid sequences |
|---|---|
| M2e | SLLTEVETPIRNEWGCRCNDSSD (SEQ ID No: 1) |
| M2eC16 | SLLTEVETPIRNEWCGCRCNDSSD (SEQ ID No: 2) |
| M2eC21 | SLLTEVETPIRNEWGCRCNCDSSD (SEQ ID No: 3) |
| M2eC22 | SLLTEVETPIRNEWGCRCNDCSSD (SEQ ID No: 4) |
| M2eC23 | SLLTEVETPIRNEWGCRCNDSCSD (SEQ ID No: 5) |
| M2eC24 | SLLTEVETPIRNEWGCRCNDSSCD (SEQ ID No: 6) |
| M2eC1621 | SLLTEVETPIRNEWCGCRCNCDSSD (SEQ ID No: 7) |
| M2eC2122 | SLLTEVETPIRNEWGCRCNCDCSSD (SEQ ID No: 8) |
| M2eC2123 | SLLTEVETPIRNEWGCRCNCDSCSD (SEQ ID No: 9) |
| M2eC212223 | SLLTEVETPIRNEWGCRCNCDCSCSD (SEQ ID No: 10) |
| M2eC151621 | SLLTEVETPIRNECWCGCRCNCDSSD (SEQ ID No: 11) |
| M2eC162122 | SLLTEVETPIRNEWCGCRCNCDCSSD (SEQ ID No: 12) |
| M2eC21222324 | SLLTEVETPIRNEWGCRCNCDCSCSCD (SEQ ID No: 13) |
| M2eC16212223 | SLLTEVETPIRNEWCGCRCNCDCSCSD (SEQ ID No: 14) |
| M2eC1621222324 | SLLTEVETPIRNEWCGCRCNCDCSCSCD (SEQ ID No: 15) |
| M2eC212121 | SLLTEVETPIRNEWGCRCNCCCDSSD (SEQ ID No: 16) |

(2) Mice Received Administration

Female BALB/c mice (seven weeks old, SPF, Charles River Japan Inc.) were preliminary bred under SPF condition. After about one week of preliminary breeding, an immunization test was performed.

(3) Immunization Groups (3)-1 Evaluation of Immunogenicity of M2eC Peptide which is Made up by Inserting One Cysteine Residue into M2e Twenty four mice were divided into six groups each consisting of four mice. Each group was immunized with M2e or each of the five M2eC peptides as shown in Table 2.

TABLE 2

| Immunization groups | Peptides (abbreviation) | No. of mice |
|---|---|---|
| Group 1 | M2e | 4 |
| Group 2 | M2eC16 | 4 |
| Group 3 | M2eC21 | 4 |
| Group 4 | M2eC22 | 4 |
| Group 5 | M2eC23 | 4 |
| Group 6 | M2eC24 | 4 |

(3)-2 Evaluation of Immunogenicity of M2eC Peptides which is Made Up by Inserting Up to 3 Cysteine Residues into M2e Twenty four mice were divided into six groups each consisting of four mice. Each group was immunized with M2e or each of the five M2eC peptides as shown in Table 3.

TABLE 3

| Immunization groups | Peptides (abbreviation) | No. of mice |
|---|---|---|
| Group 1 | M2e | 4 |
| Group 2 | M2eC21 | 4 |
| Group 3 | M2eC1621 | 4 |
| Group 4 | M2eC2122 | 4 |
| Group 5 | M2eC2123 | 4 |
| Group 6 | M2eC212223 | 4 |

(3)-3 Evaluation of Immunogenicity of M2eC Peptides which is Made Up by Inserting 3 or More Cysteine Residues into M2e Thirty two mice were divided into eight groups each consisting of four mice. Each group was immunized with M2e or each of the seven M2eC peptides as shown in Table 4.

TABLE 4

| Immunization groups | Peptides (abbreviation) | No. of mice |
|---|---|---|
| Group 1 | M2e | 4 |
| Group 2 | M2eC212223 | 4 |
| Group 3 | M2eC151621 | 4 |
| Group 4 | M2eC162122 | 4 |
| Group 5 | M2eC21222324 | 4 |
| Group 6 | M2eC16212223 | 4 |
| Group 7 | M2eC1621222324 | 4 |
| Group 8 | M2eC212121 | 4 |

(4) Preparation of Immune Substance

On the previous day of immunization, each peptide stock solution stored at below −80° C. was diluted at 1 mg/mL with PBS (INVITROGEN) and mixed with an equal amount of Alum adjuvant (ALHYDROGEL, BRENNTAG BIOSECTOR), and the mixture was left to stand overnight.

(5) Immunization Protocol and Schedule

Each immunizing material prepared on the previous day was diluted at 0.2 mg/mL with PBS, and each 100 μL per mouse of the material was subcutaneously administered to the back of mice by using 1 mL tuberculin syringe (Terumo, SS-01T2613S) (dose per individual: each peptide 20 μg). Immunization was performed twice at an interval of two weeks.

(6) Blood Collection

Two weeks after the second immunization, all the mice were subject to blood collection from the lower abdominal vein while anesthetized with pentobarbital sodium (Kyoritsu Seiyaku Corporation, somnopentyl) and were sacrificed. The obtained blood was transferred to Microtina (Becton Dickinson), and after sufficiently clotting at room temperature, centrifuged at 5,000 rpm×10 min. to isolate serum. The isolated serum was stored at −20° C. until measure.

(7) Preparation of Mouse Standard Serum

For comparing an increased anti-M2e antibody in each immunization group, sera from 15 mice that were subcutaneously immunized at the back with M2e shown in Table 1 (10 μg/body/shot) and Alum adjuvant three times at an interval of three weeks were pooled as mouse standard serum having an anti-M2e antibody.

(8) Measurement of Anti-M2e Antibody (IgG)

M2e was diluted at 2 μg/mL with 0.1M Carbonate buffer, pH9.6, added to 96-well plate (Nunc, Immobilizer Amino) at 100 µL/well and left to stand at 4° C. overnight for immobilization. On the following day, each well was washed with 300 µL of 0.05% Tween 20 containing phosphate buffer (PBST) three times, added with each 300 µL/well of mM monoethanolamine (Wako Pure Chemical Industries, Ltd.) diluted with 0.1M Carbonate buffer, pH9.6, and left to stand at room temperature for one hour.

After one hour, 10 mM monoethanolamine was sufficiently removed, and 100 µL/well of samples diluted with PBST were added thereto (in duplicate for each sample). After the reaction at room temperature for one hour, each diluted serum was removed and washed with 300 µL/well of PBST three times. After washing, the wash solution in each well was sufficiently removed and an HRP-labeled anti-mouse IgG goat antibody (American Qualax, A131PS) diluted with PBST 2,000 folds was added at 100 µL/well for the reaction at room temperature for one hour. After the reaction, the diluted solution comprising the labeled antibody was removed, and the well was washed with 300 µL/well of PBST twice and an equal volume of distilled water twice, and added with a chromogenic substrate solution TMB+ (Dako) at 100 µL/well under light shielding for the reaction at room temperature for 30 minutes. Then, the well was added with 1N sulfuric acid at 100 µL/well to stop the chromogenic reaction and absorbance at 450 nm (OD 450 value) was measured.

(9) Calculation of Anti-M2e Antibody Titer in Standard Serum

The sera from 32 non-immunized mice (C57BL/6, male) were diluted with a dilution solution for sample to 200 folds and determined for OD 450 in duplicate. An average of the measured OD 450 plus twice of their standard deviation was defined as cutoff. Then, the standard serum was diluted from 15,000 to 960,000 folds via two-fold serial dilution, determined for their OD 450, and a maximum dilution scale over cutoff value was defined as an antibody titer of the standard serum. Since the OD 450 values were over cutoff in this test system until about 400,000 folds dilution, an anti-M2e antibody titer of a stock solution of the standard serum was determined 400,000 units.

(10) Anti-M2e Antibody Titer in Blood

An antibody titer of mouse serum in each group immunized with each of the various peptides was calculated as described below. First, the standard serum was diluted with a dilution solution for sample to give 1, 2, 4, 8, 16 and 32 units to prepare standard for determination of an antibody titer. Next, mouse serum of each immunization group was diluted with a dilution solution for sample such that the diluted serum may be within a scope of the standard as prepared. The test sample prepared as described above was determined in the system as shown in Example 1-(8) and an anti-M2e antibody titer of each serum sample in mouse was calculated by using a standard line between the obtained standard unit and the OD 450 value.

2. Results

FIG. 1 shows anti-M2e antibody titers in blood obtained two weeks after twice immunization at an interval of two weeks in immunization groups for M2e or each M2eC peptide in which one cysteine residue is inserted. As shown in FIG. 1, except for the M2eC22 peptide in which one cysteine residue is inserted at position between No. 21 and No. 22 of M2e, an anti-M2e antibody titer of M2eC peptide immunization group was increased from two to four folds as compared to that of M2e immunization groups.

As a result, it proved that peptides in which one cysteine residue is inserted at one position either between No. 15 and No. 16, between No. 20 and No. 21, between No. and No. 23 or between No. 23 and No. 24 of M2e have higher immunogenicity as compared to that of the conventional M2e peptide.

Figure 2:
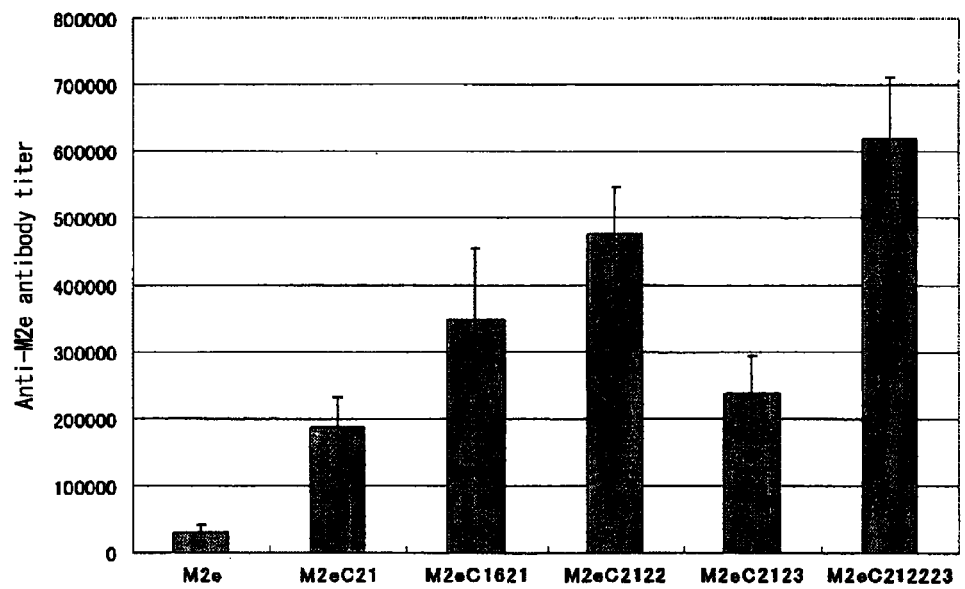
FIG. 2 is a graph showing mean anti-M2e antibody titers of the respective immunization groups shown in Table 3.

Next, immunogenicity of M2eC peptides in which two or three cysteine residues are inserted was evaluated by using an anti-M2e antibody titer. As shown in FIG. 2, it was confirmed that M2eC1621, M2eC2122 and M2eC2123 in which two cysteine residues are inserted into M2e, i.e. in which one cysteine residue is further inserted in M2eC21 in which cysteine residue is inserted at position between No. and No. 21, had an increased anti-M2e antibody titer than M2eC21. In addition, the immunization group of M2eC212223 in which each one cysteine residue is inserted in positions between No. 20 and No. 21, between No. 21 and No. 22 and between No. 22 and No. 23 of M2e, i.e. in which a total of three cysteine residues are inserted, showed extremely high immunogenicity, i.e. an anti-M2e antibody titer was 20 times higher than that of the immunization groups of M2e.

Figure 3:
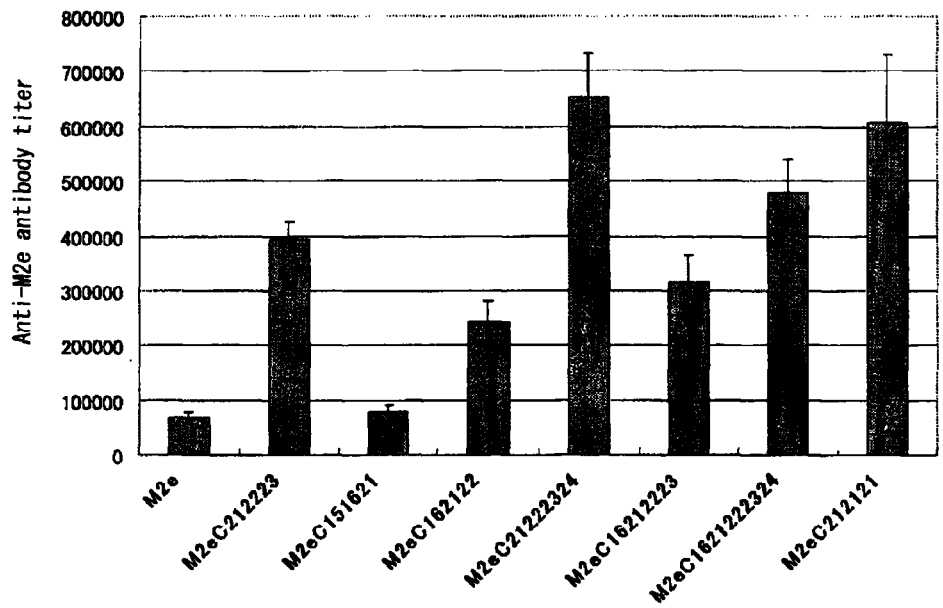
FIG. 3 is a graph showing mean anti-M2e antibody titers of the respective immunization groups shown in Table 4.

Similarly, immunogenicity of the M2eC peptide in which an increased number of cysteine residues are inserted was evaluated by an anti-M2e antibody titer. As shown in FIG. 3, M2eC162122 in which three cysteine residues are inserted could induce a higher antibody titer than that of M2e likewise M2eC212223. However, M2eC151621 in which three cysteine residues are similarly inserted could only induce an antibody titer comparable to M2e. From this, it is estimated that an epitope of M2e might be affected by inserting cysteine residue at position between No. 14 and No. 15.

Furthermore, anti-M2e antibodies in the M2eC16212223 or M2eC1621222324 immunization groups were higher than that of M2eC162122, and an anti-M2e antibody titer in M2eC21222324 immunization group was higher than that of M2eC212223. This suggests that immunogenicity might be enhanced by increasing the number of cysteine residues to be inserted. In addition, since the M2eC212121 immunization group in which a total number of three cysteine residues are inserted at position between 20 and 21 of M2e also induced a high anti-M2e antibody titer, it may be conceivable that immunogenicity might be enhanced by inserting multiple cysteine residues at position between 15 and 16, between 20 and 21, between 22 and 23 or between 23 and 24, insertion of cysteine residue(s) at which position is proved to increase an anti-M2e antibody titer.

In view of the above results, it was noted that M2eC peptide could be a more potent influenza vaccine by increasing the number of cysteine residues to be inserted into M2e.

Example 2

Evaluation of an Ability of Protecting Onset of Disease in M2eC Peptide

1. Materials and Methods
(1) Peptides
Among the M2eC peptides used in Example 1, M2eC212223 was used.
(2) Challenge Virus
Influenza virus (A/PR8/8/34 strain, H1N1) stored by freezing was used.
(3) Mice Received Administration
The same procedures as in Example 1-(2) were performed.
(4) Immunization Groups
Thirty mice were divided into three groups each consisting of 10, 8 and 12 mice. Mice in the first and the second groups were immunized with 2 µg and 20 µg of M2eC212223, respectively, and mice in the third group were not immunized as peptide non-administration group as shown in Table 5.

TABLE 5

| Immunization groups | Peptide (abbreviation) | Amount of immunizing peptide | No. of mice |
|---|---|---|---|
| Group 1 | M2eC212223 | 2 µg | 10 |
| Group 2 | M2eC212223 | 20 µg | 8 |
| Group 3 | none | 0 µg | 12 |

(5) Preparation of Immunizing Material and Protocol and Schedule of Immunization For priming, on the day of immunization, M2eC212223 stock solution under storage at below −60° C. was diluted at 0.04 mg/mL and 0.4 mg/mL with PBS (INVITROGEN), mixed with an equal amount of complete Freund's adjuvant, each 100 µL per mouse of the mixture was subcutaneously administered to the back of mice with 1 mL tuberculin syringe (Terumo, SS-01T2613S) (dose per individual: 2 µg or 20 µg). For the third group as control, PBS was used in place of the peptide solution. For the second immunization, the procedures as in the priming were repeated provided that incomplete Freund's adjuvant was used for adjuvant. Immunization was performed twice at an interval of two weeks.

(6) Preparation of Virus Solution for Challenge and Way to Challenge

One week after the second immunization, a solution of influenza virus (A/PR8 strain) stored by freezing was diluted with PBS and nasally administered to mice anesthetized with Sevofrane (Maruishi Pharmaceutical) at 20 µL (corresponding to 5 $LD_{50}$) per mouse.

(7) Observation of Mice

Test mice were observed until 21 days after the virus challenge to record their life and death.

2. Results

As a result of the observation of mice after challenge of influenza virus, the M2eC212223 immunization group in which each one cysteine residue is inserted at positions between No. 20 and No. 21, between No. 21 and No. 22 and between No. 22 and No. 23 of M2e, i.e. in which a total of three cysteine residues are inserted, showed a survival rate higher than that of peptide non-administration group as shown in Table 6. This result revealed that M2eC212223 peptide, even by immunization of 2 µg per mouse, had an inhibiting effect to onset of disease by influenza virus.

TABLE 6

| Immunization groups | Peptide (abbreviation) | Amount of immunizing peptide | Survival rate |
|---|---|---|---|
| Group 1 | M2eC212223 | 2 µg | 8/10 |
| Group 2 | M2eC212223 | 20 µg | 7/8 |
| Group 3 | none | 0 µg | 4/12 |

Example 3

Comparison of an Ability of Protecting Onset of Disease Between M2e and M2eC212223 Peptides Against Homologous and Heterologous Virus Challenge Systems 1. Materials and Methods (1) Peptide Used in Immunization and Challenge Virus M2e and M2eC212223 in Example 1 were used for immunization in homologous virus challenge system whereas swM2e and swM2eC212223, synthesized on the basis of M2 sequence of a new strain of influenza virus (A/H1N1 type) which occurred in epidemics in 2009, were used for immunization in heterologous virus challenge system (BEX Co., Ltd.). Stock solutions of the synthesized peptides were prepared as described in Example 1 and stored at below −60° C. until use. The challenge virus was the same as used in Example 2.

Table 7 indicates M2e sequences of peptides used in immunization and of the challenge virus. In homologous virus challenge system, there is difference of only one amino acid at position No. 21 between the M2e sequence of the challenge virus and the sequences of the immunizing peptides. However, for heterologous virus challenge system, amino acids at five positions No. 11, No. 13, No. 16, No. 20 and No. 21 are different.

TABLE 7

| Challenge system | Virus or peptides | Amino acid sequence |
|---|---|---|
| Homologous | Challenge virus (A/PR8) | SLLTEVETPIRNEWGCRCN<u>G</u>SSD (SEQ ID No: 17) |
| | M2e | SLLTEVETPIRNEWGCRCNDSSD (SEQ ID No: 1) |
| | M2eC212223 | SLLTEVETPIRNEWGCRCNCDCSCSD (SEQ ID No: 10) |
| Heterologous | Challenge virus (A/PR8) | SLLTEVETP<u>IR</u>NEWGCRC<u>NG</u>SSD (SEQ ID No: 17) |
| | swM2e | SLLTEVETPTRSEWECRCSDSSD (SEQ ID No: 18) |
| | swM2eC212223 | SLLTEVETPTRSEWECRCSCDCSCSD (SEQ ID No: 19) |

* Underlined amino acids are those different from peptides used in immunization.

(2) Mice Received Administration

The same procedures as in Example 1-(2) were performed.

(3) Immunization Groups (3)-1 Evaluation of an Ability of Protecting Onset of Disease in Homologous Virus Challenge System Twenty four mice were divided into three groups each consisting of eight mice. Mice in the first and the second groups were immunized with M2e and M2eC212223 peptide, respectively, and mice in the third group were administered PBS in place of peptide as peptide non-administration group (Alum only group) as shown in Table 8.

TABLE 8

| Immunization groups | Peptide (abbreviation) | Amount of immunizing peptide | No. of mice |
|---|---|---|---|
| Group 1 | M2e | 2 µg | 8 |
| Group 2 | M2eC212223 | 2 µg | 8 |
| Group 3 | none | 0 µg | 8 |

(3)-2 Evaluation of an Ability of Protecting Onset of Disease in Heterologous Virus Challenge System Sixty mice were divided into six groups each consisting of ten mice. Mice in the first and the second groups were immunized with swM2e, mice in the third and the fourth groups were immunized with swM2eC212223 peptide, and mice in the fifth and the sixth groups were not immunized as peptide non-administration groups as shown in Table 9. Mice in the fifth groups were administered with Alum adjuvant alone and mice in the sixth groups were administered with PBS alone.

TABLE 9

| Immunization groups | Peptide (abbreviation) | Amount of immunizing peptide | No. of mice |
|---|---|---|---|
| Group 1 | swM2e | 2 μg | 10 |
| Group 2 | swM2e | 20 μg | 10 |
| Group 3 | swM2eC212223 | 2 μg | 10 |
| Group 4 | swM2eC212223 | 20 μg | 10 |
| Group 5 | none | 0 μg | 10 |
| Group 6 | none | 0 μg | 10 |

(4) Preparation of Immunizing Material and Protocol and Schedule of Immunization (4)-1 Evaluation of an Ability of Protecting Onset of Disease in Homologous Virus Challenge System On the previous day of immunization, a peptide stock solution was prepared as described in Example 1-(4). On the following day, each prepared immunizing material was diluted at 0.02 mg/mL with PBS, and each 100 μL per mouse of the material was subcutaneously administered to the back of mice with 1 mL tuberculin syringe (Terumo, SS-01T2613S) (dose per individual: each peptide 2 μg). Immunization was performed twice at an interval of two weeks. On the previous day of virus challenge (6 days after the second immunization), partial blood collection was performed via tail vein in mice to isolate serum as described in Example 1-(6), which was stored at −20° C. until determination of an anti-M2e antibody titer.

(4)-2 Evaluation of an Ability of Protecting Onset of Disease in Heterologous Virus Challenge System On the previous day of immunization, a peptide stock solution was prepared as described in Example 1-(4).

On the following day, each prepared immunizing material was diluted at 0.02 mg/mL or 0.2 mg/mL with PBS, and each 100 μL per mouse of the material was subcutaneously administered to the back of mice with 1 mL tuberculin syringe (Terumo, SS-01T2613S) (dose per individual: each peptide 2 μg or 20 μg). Immunization was performed twice at an interval of two weeks, and serum was obtained and stored on the previous day of virus challenge as described in Example 3-(4)-1.

(5) Anti-M2e Antibody Titer in Blood

Determination of an anti-M2e antibody titer in serum in each test mice was performed as described in Example 1.

(6) Preparation of Virus Solution for Challenge and Way to Challenge

The procedures as described in example 2 were repeated.

(7) Observation of Mice

Test mice were observed until 21 days after the virus challenge to record their life and death.

2. Results

Figure 4:
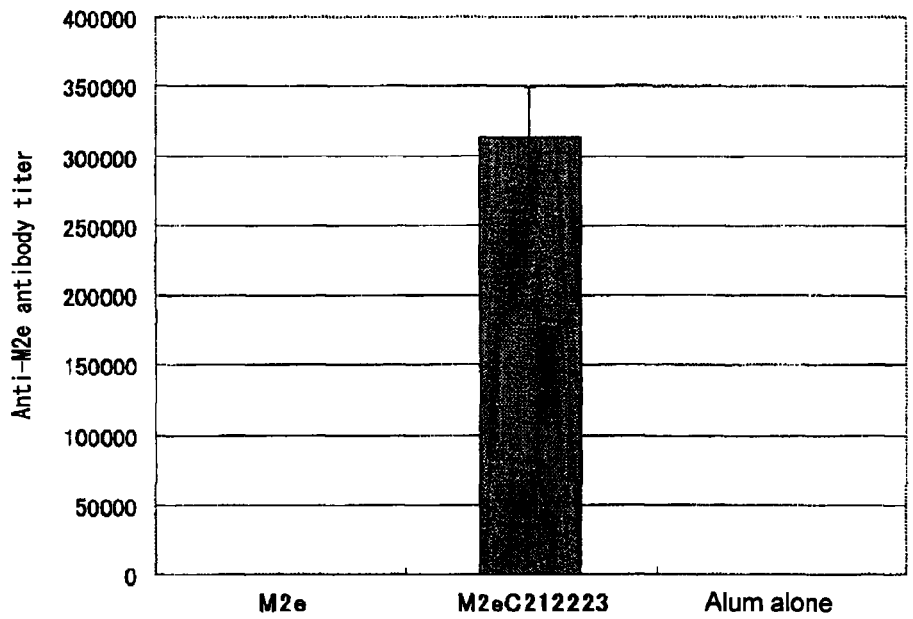
FIG. 4 is a graph showing mean anti-M2e antibody titers just before challenge with homologous virus challenge system.

For homologous virus challenge system, as shown in FIG. 4, the immunization group with 2 μg of M2eC212223 together with Alum adjuvant, which admitted for use in human, could induce a high anti-M2e antibody titer (an antibody against a peptide having a sequence similar to the M2e sequence of the challenge virus). However, the immunization group with M2e in which cysteine residue is not inserted could not induce an anti-M2e antibody titer at a dose of 2 μg. As for the results obtained after virus challenge, as shown in Table 10, the M2eC212223 immunization group had a significantly higher survival rate as compared to the M2e immunization group and the peptide non-administration group. This result revealed that the M2eC212223 peptide together with Alum adjuvant, which is admitted for use in human, had a high protective effect to onset of disease against challenge of influenza virus having a sequence similar to that of the M2eC212223 peptide. Also, it proved that the M2eC212223 peptide had a higher ability of protecting onset of disease as compared to M2e peptide In view of the above results, it was noted that M2eC peptide in which cysteine residue(s) is/are inserted into the M2e peptide has high immunogenicity and a high protective effect against influenza virus infection, as compared to the M2e peptide and thus may preferably be used as material of a vaccine.

TABLE 10

| Immunization groups | Peptide (abbreviation) | Survival rate |
|---|---|---|
| Group 1 | M2e | 3/8 |
| Group 2 | M2eC212223 | 6/8 |
| Group 3 | none | 1/8 |

Figure 5:
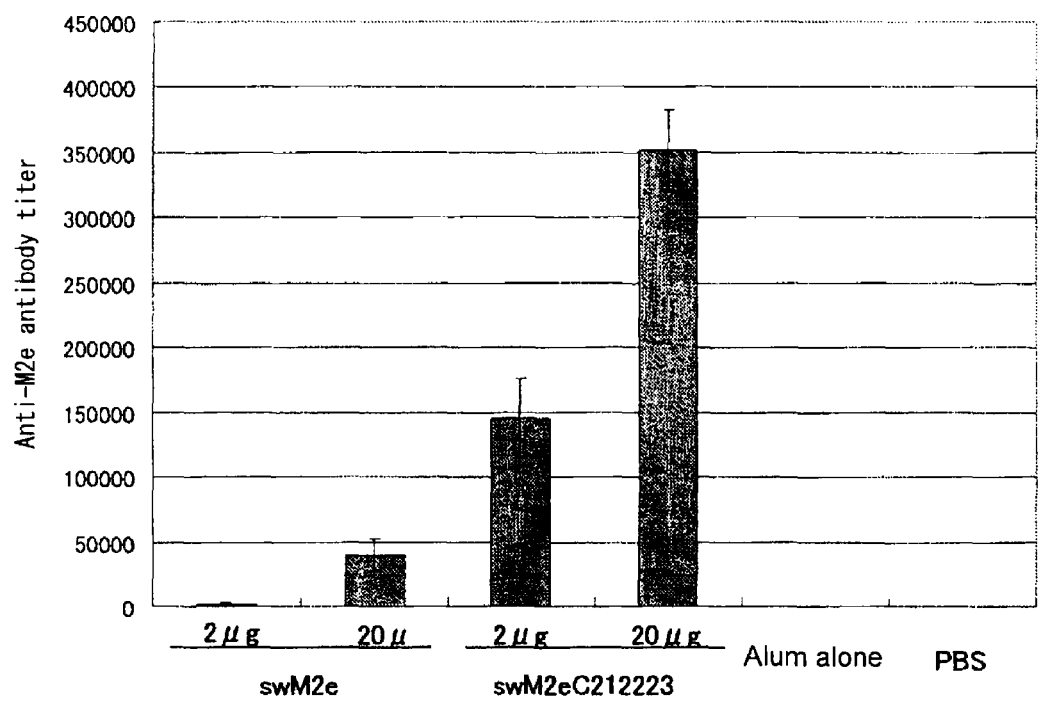
FIG. 5 is a graph showing mean anti-M2e antibody titers just before challenge with heterologous virus challenge system.

For heterologous virus challenge system, as shown in FIG. 5, an anti-M2e antibody titer immediately before challenge (an antibody against a peptide having a sequence similar to the M2e sequence of the challenge virus) was the highest in the immunization group with 20 μg of swM2eC212223, followed by the immunization group with 2 μg of swM2eC212223, and then the immunization group with 20 μg of swM2e, but almost no increase in an antibody titer was observed in the immunization group with 2 μg of swM2e. In addition, a survival rate of mice after virus challenge, as shown in Table 11, corresponds to the increased anti-M2e antibody titer described above and thus a protective effect to onset of disease was confirmed in the immunization groups with 20 μg of swM2e and the swM2eC212223 immunization group with 2 μg and 20 μg, which showed a high anti-M2e antibody titer. Thus, it was revealed that the swM2eC212223 peptide, in which cysteine residues are inserted, which can induce a high anti-M2e antibody may provide an ability of protection against influenza virus infection at a lower amount as compared to the swM2e peptide in which cysteine residue is not inserted.

In view of the above results, it was noted that the M2eC peptide in which cysteine residue(s) is/are inserted into the M2e peptide has high protective effect against infection of influenza virus having mutation, and thus may preferably be used as material of a vaccine.

TABLE 11

| Immunization groups | Peptide (abbreviation) | Survival rate |
|---|---|---|
| Group 1 | swM2e | 4/10 |
| Group 2 | swM2e | 8/10 |
| Group 3 | swM2eC212223 | 9/9 |
| Group 4 | swM2eC212223 | 7/8 |
| Group 5 | none | 4/10 |
| Group 6 | none | 4/10 |

INDUSTRIAL APPLICABILITY

The modified peptide of the present invention may be utilized as a universal influenza vaccine against influenza virus type A.

The invention claimed is:

1. A modified influenza virus Matrix 2 peptide obtained by inserting only one or more cysteine residues into an influenza virus Matrix 2 peptide between positions 15 to 24 of the influenza Matrix 2 peptide, wherein positions 15 to 24 correspond to positions 14 to 23 of SEQ ID NO: 1.

2. The modified influenza virus Matrix 2 peptide of claim 1, wherein the influenza virus Matrix 2 peptide is from an influenza virus type A.

3. The modified peptide of claim 1, wherein the one or more cysteine residues is inserted at either one or a combination of two or more of positions between positions No. 15 and No. 16, positions No. 20 and No. 21, positions No. 21 and No. 22, positions No. 22 and No. 23 and positions No. 23 and No. 24 of the influenza virus Matrix 2 peptide corresponding to positions No. 14 and No. 15, positions No. 19 and No. 20, positions No. 20 and No. 21, positions No. 21 and No. 22 and positions No. 22 and No. 23 of SEQ ID NO: 1, respectively.

4. The modified influenza virus Matrix 2 peptide of claim 1, wherein a total number of the one or more cysteine residues inserted is 1 to 5.

5. The modified influenza virus Matrix 2 peptide of claim 4, wherein a total number of the one or more cysteine residues inserted on each inserted position is up to 3.

6. An isolated fusion protein, comprising the modified influenza virus Matrix 2 peptide of claim 1 and a polypeptide.

7. The isolated fusion protein of claim 6, wherein the polypeptide is annexin V or albumin.

8. An influenza immunogenic composition comprising the modified influenza virus Matrix 2 peptide of claim 1.

9. A device comprising the influenza immunogenic composition of claim 8, wherein the device can be delivered into the body across a biological barrier.

10. An influenza immunogenic composition comprising the fusion protein of claim 6.

* * * * *

SEQUENCE LISTING

<160> NUMBER OF SEQ ID NOS: 20

<210> SEQ ID NO 1
<211> LENGTH: 23
<212> TYPE: PRT
<213> ORGANISM: Influenza A virus

<400> SEQUENCE: 1

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      modified peptide obtained by inserting a cysteine
      into the peptide derived from Influenza virus M2
      protein

<400> SEQUENCE: 2

Ser Leu Leu Thr Glu Val Glu Thr Pro Ile Arg Asn Glu Trp Cys Gly
1               5                   10                  15

Cys Arg Cys Asn Asp Ser Ser Asp
            20

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      modified peptide obtained by inserting a cysteine
      into the peptide derived from Influenza virus M2
      protein

<400> SEQUENCE: 3

Ser Leu Leu Thr Glu Val Glu Thr Pro Ile Arg Asn Glu Trp Gly Cys
1               5                   10                  15

Arg Cys Asn Cys Asp Ser Ser Asp
            20

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      modified peptide obtained by inserting a cysteine
      into the peptide derived from Influenza virus M2
      protein

<400> SEQUENCE: 4

Ser Leu Leu Thr Glu Val Glu Thr Pro Ile Arg Asn Glu Trp Gly Cys
1               5                   10                  15

Arg Cys Asn Asp Cys Ser Ser Asp
            20

<210> SEQ ID NO 5
<211> LENGTH: 24
<212> TYPE: PRT
<213> ORGANISM: Artificial Sequence
<220> FEATURE:

```
<223> OTHER INFORMATION: Description of Artificial Sequence: Synthetic
      modified peptide obtained by inserting a cysteine
      into the peptide derived from Influenza virus M2
      protein

<400> SEQUENCE: 5

Ser Leu Leu Thr Glu Val Glu Thr Pro Ile Arg Asn Glu Trp Gly Cys
1               5                   10                  15

Arg Cys Asn Asp Ser Cys Ser Asp
            20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      modified peptide obtained by inserting a cysteine
      into the peptide derived from Influenza virus M2
      protein

<400> SEQUENCE: 6

Ser Leu Leu Thr Glu Val Glu Thr Pro Ile Arg Asn Glu Trp Gly Cys
1               5                   10                  15

Arg Cys Asn Asp Ser Ser Cys Asp
            20

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 7

Ser Leu Leu Thr Glu Val Glu Thr Pro Ile Arg Asn Glu Trp Cys Gly
1               5                   10                  15

Cys Arg Cys Asn Cys Asp Ser Ser Asp
            20                  25

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 8

Ser Leu Leu Thr Glu Val Glu Thr Pro Ile Arg Asn Glu Trp Gly Cys
1               5                   10                  15

Arg Cys Asn Cys Asp Cys Ser Ser Asp
            20                  25

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
``` protein

<400> SEQUENCE: 9

Ser Leu Leu Thr Glu Val Glu Thr Pro Ile Arg Asn Glu Trp Gly Cys
1               5                   10                  15

Arg Cys Asn Cys Asp Ser Cys Ser Asp
            20                  25

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 10

Ser Leu Leu Thr Glu Val Glu Thr Pro Ile Arg Asn Glu Trp Gly Cys
1               5                   10                  15

Arg Cys Asn Cys Asp Cys Ser Cys Ser Asp
            20                  25

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 11

Ser Leu Leu Thr Glu Val Glu Thr Pro Ile Arg Asn Glu Cys Trp Cys
1               5                   10                  15

Gly Cys Arg Cys Asn Cys Asp Ser Ser Asp
            20                  25

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 12

Ser Leu Leu Thr Glu Val Glu Thr Pro Ile Arg Asn Glu Trp Cys Gly
1               5                   10                  15

Cys Arg Cys Asn Cys Asp Cys Ser Ser Asp
            20                  25

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 13

```
Ser Leu Leu Thr Glu Val Glu Thr Pro Ile Arg Asn Glu Trp Gly Cys
1               5                   10                  15

Arg Cys Asn Cys Asp Cys Ser Cys Ser Cys Asp
            20                  25

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 14

Ser Leu Leu Thr Glu Val Glu Thr Pro Ile Arg Asn Glu Trp Cys Gly
1               5                   10                  15

Cys Arg Cys Asn Cys Asp Cys Ser Cys Ser Asp
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 15

Ser Leu Leu Thr Glu Val Glu Thr Pro Ile Arg Asn Glu Trp Cys Gly
1               5                   10                  15

Cys Arg Cys Asn Cys Asp Cys Ser Cys Ser Cys Asp
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 16

Ser Leu Leu Thr Glu Val Glu Thr Pro Ile Arg Asn Glu Trp Gly Cys
1               5                   10                  15

Arg Cys Asn Cys Cys Cys Asp Ser Ser Asp
            20                  25

<210> SEQ ID NO 17
<211> LENGTH: 23
<212> TYPE: PRT
<213> ORGANISM: Influenza A virus

<400> SEQUENCE: 17

Ser Leu Leu Thr Glu Val Glu Thr Pro Ile Arg Asn Glu Trp Gly Cys
1               5                   10                  15

Arg Cys Asn Gly Ser Ser Asp
            20
```

```
<210> SEQ ID NO 18
<211> LENGTH: 23
<212> TYPE: PRT
<213> ORGANISM: Influenza A virus

<400> SEQUENCE: 18

Ser Leu Leu Thr Glu Val Glu Thr Pro Thr Arg Ser Glu Trp Glu Cys
1               5                   10                  15

Arg Cys Ser Asp Ser Ser Asp
            20

<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Synthetic
      modified peptide obtained by inserting cysteines
      into the peptide derived from Influenza virus M2
      protein

<400> SEQUENCE: 19

Ser Leu Leu Thr Glu Val Glu Thr Pro Thr Arg Ser Glu Trp Glu Cys
1               5                   10                  15

Arg Cys Ser Cys Asp Cys Ser Cys Ser Asp
            20                  25

<210> SEQ ID NO 20
<211> LENGTH: 23
<212> TYPE: PRT
<213> ORGANISM: Influenza A virus
<220> FEATURE:
<221> NAME/KEY: MOD_RES
<222> LOCATION: (2)..(2)
<223> OTHER INFORMATION: Pro or Leu
<220> FEATURE:
<221> NAME/KEY: MOD_RES
<222> LOCATION: (10)..(10)
<223> OTHER INFORMATION: Ile or Thr
<220> FEATURE:
<221> NAME/KEY: MOD_RES
<222> LOCATION: (12)..(12)
<223> OTHER INFORMATION: Asn or Ser
<220> FEATURE:
<221> NAME/KEY: MOD_RES
<222> LOCATION: (13)..(13)
<223> OTHER INFORMATION: Gly or Glu
<220> FEATURE:
<221> NAME/KEY: MOD_RES
<222> LOCATION: (15)..(15)
<223> OTHER INFORMATION: Gly or Glu
<220> FEATURE:
<221> NAME/KEY: MOD_RES
<222> LOCATION: (17)..(17)
<223> OTHER INFORMATION: Lys or Arg
<220> FEATURE:
<221> NAME/KEY: MOD_RES
<222> LOCATION: (19)..(19)
<223> OTHER INFORMATION: Asn or Ser
<220> FEATURE:
<221> NAME/KEY: MOD_RES
<222> LOCATION: (20)..(20)
<223> OTHER INFORMATION: Gly or Asp
<220> FEATURE:
<221> NAME/KEY: MOD_RES
<222> LOCATION: (22)..(22)
<223> OTHER INFORMATION: Asn or Ser

<400> SEQUENCE: 20

Ser Xaa Leu Thr Glu Val Glu Thr Pro Xaa Arg Xaa Xaa Trp Xaa Cys
1               5                   10                  15
```

```
Xaa Cys Xaa Xaa Ser Xaa Asp
                20
```